United States Patent [19]

Ikeda et al.

[11] Patent Number: 5,202,467
[45] Date of Patent: Apr. 13, 1993

[54] PROCESS FOR PREPARING HALOKETO ACID DERIVATIVES

[75] Inventors: Takaharu Ikeda, Ibaraki; Seiichi Kai, Nara; Masayoshi Minai, Moriyama, all of Japan

[73] Assignee: Sumitomo Chemical Company, Limited, Osaka, Japan

[21] Appl. No.: 651,971

[22] Filed: Feb. 7, 1991

[30] Foreign Application Priority Data

Feb. 8, 1990 [JP] Japan .................. 2-30013
Feb. 8, 1990 [JP] Japan .................. 2-30014

[51] Int. Cl.$^5$ .................. C07C 69/675; C07C 59/76
[52] U.S. Cl. .................. 560/174; 562/577
[58] Field of Search .................. 560/174; 562/577

[56] References Cited

U.S. PATENT DOCUMENTS 4,334,087  6/1982  Baer et al. .................. 562/459

FOREIGN PATENT DOCUMENTS 0048025  3/1982  European Pat. Off. .
0048301  3/1982  European Pat. Off. .
0161546  11/1985  European Pat. Off. .
3401913  8/1985  Fed. Rep. of Germany .

OTHER PUBLICATIONS

W. Theilheimer: "Synthetic Methods of Organic Chemistry Vol. 4", 1966, S. Karger, Basel, CH, p. 158, reaction 448, IBID vol. 6, 1952, pp. 305-306, reaction 823, IBID vol. 7, 1953, p. 199, reaction 511, IBID vol. 20, 1966, p. 307, reaction 370.
Houben-Weyl: "Methoden der Organischen Chemie vol. VII/2a 4th edition" 1973, Georg Thieme Verlag, Stuttgart DE, p. 800, 1,4-7; p. 804, par. 1.
J. March: "Advanced Organic Chemistry 2nd edition" (1977), McGraw Hill Int'l, Auckland AU, p. 419, par. 3-p, 420, par. 1.
J. Chem. Soc., 107, Synthesis of α-Tetronic Acid, by Kletz and Lapworth, pp. 1254-1265.
Chemical Abstr., 1957, 3457 (abstract of Bull. soc. chim. France 1956, 1361-1363).
J. Org. Chem. vol. 37, No. 3, 1972, 505-506.
J. Org. Chem. vol. 36, No. 23, 1971, 3553-3560.
J. Med. Chem. 1987, 30, 1074-1090.

*Primary Examiner*—Arthur C. Prescott
*Attorney, Agent, or Firm*—Birch, Stewart, Kolasch & Birch

[57] ABSTRACT

Process for preparing haloketo acid derivatives [I]:

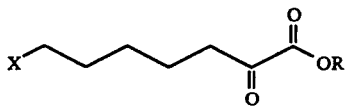

wherein R is H or $C_{1-6}$ alkyl, and X is chlorine or bromine, which comprises reacting β-oxo-acid ester [II]:

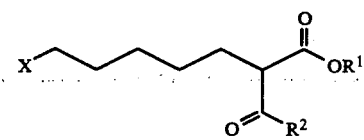

wherein $R^1$ is $C_{1-6}$ alkyl, $R^2$ is $C_{1-5}$ alkyl or $OR^3$ ($R^3$ is $C_{1-6}$ alkyl), and X is the same as above, with nitrosating agent [IV]:

ONOR$^4$  [IV]

wherein $R^4$ is H, alkyl, halogen or $SO_3H$ to give 7-halo-2-hydroxyiminoheptanoic acid ester [III]:

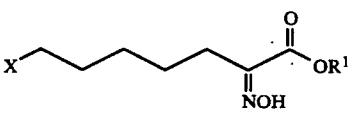

wherein $R^1$ and X are the same as above, followed by reacting the product with aldehyde or ketone; and intermediates therefor, and process for preparing said intermediates. Said haloketo acid derivatives are useful as intermediate for synthesis of cilastatin, which is useful as medicament, especially as dehydropeptidase inhibitor.

26 Claims, No Drawings

PROCESS FOR PREPARING HALOKETO ACID DERIVATIVES

The present invention relates to a process for preparing haloketo acid derivatives which are intermediates for synthesis of cilastatin, the said cilastatin being useful as a medicament, especially as a dehydropeptidase inhibitor. More particularly, it relates to a process for preparing haloketo acid derivatives of the formula [I]:

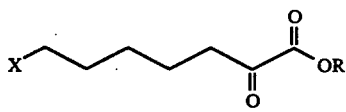

wherein R is hydrogen atom or an alkyl group having 1 to 6 carbon atoms, X is chlorine atom or bromine atom, and novel intermediates therefor.

PRIOR ART

The haloketo acid derivatives [I] have been known as an intermediate for synthesis of cilastatin (cf. J. Med. Chem. 1987, 30, 1074), and there are known some processes for preparing the same, for example, (a) a process comprising reacting a 1-bromo-5-halopentane with magnesium, followed by reacting the product with diethyl oxalate (cf. Japanese Patent First Publication No. 248612/1985), or (b) a process comprising reacting a 1,3-dithiane derivative with a 1,5-dibromopentane (cf. J. Med. Chem. 1987, 30, 1074).

However, these processes are not satisfactory for the production of the compounds [I] on industrial scale, because these processes strictly need to control the presence of moisture, and in the process (a), the recovery of solvent in high purity is difficult, and in the process (b), the starting material, 1,3-dithiane derivatives are expensive.

BRIEF DESCRIPTION OF THE INVENTION

An object of the present invention is to provide an industrially advantageous process for preparing haloketo acid derivatives [I] with solving the above mentioned problems. Another object of the present invention is to provide novel $\beta$-oxo-acid esters [II] and 7-halo-2-hydroxyiminoheptanoic acid esters [III], which are useful for preparing the above haloketo acid derivative [I], and a process for preparing these intermediates [II] and [III].

DETAILED DESCRIPTION OF THE INVENTION

The present invention relates to a process for preparing haloketo acid derivatives [I], which comprises reacting a $\beta$-oxo-acid ester of the formula [II]:

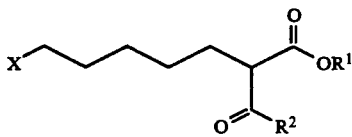

wherein $R^1$ is an alkyl group having 1 to 6 carbon atoms, $R^2$ is an alkyl group having 1 to 5 carbon atoms, or a group of the formula: $OR^3$ (wherein $R^3$ is an alkyl group having 1 to 6 carbon atoms), and X is chlorine atom or bromine atom, with a nitrosating agent of the formula [IV]:

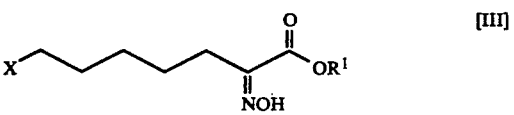

wherein $R^4$ is hydrogen atom, an alkyl group having 1 to 12 carbon atoms, a halogen atom or a group of the formula: $SO_3H$ to give a 7-halo-2-hydroxyiminoheptanoic acid ester of the formula [III]:

$$X\text{-}(CH_2)_5\text{-}C(=NOH)\text{-}C(=O)OR^1 \quad [III]$$

wherein $R^1$ and X are the same as defined above, followed by reacting the compound [III] with an aldehyde compound or a ketone compound in the presence of an acid, and further relates to intermediates therefor, and a process for preparing the intermediates.

In the reaction between a $\beta$-oxo-acid ester [II] and a nitrosating agent [IV] to give a 7-halo-2-hydroxyiminopentanoic acid ester [III], the $\beta$-oxo-acid ester [II] is, for example, $\beta$-keto acid esters (e.g. 7-halo-2-(1-oxoethyl)heptanoic acid ester, 7-halo-2-(1-oxopropyl)heptanoic acid ester, 7-halo-2-(1-oxobutyl)heptanoic acid ester, 7-halo-2-(1-oxopentyl)heptanoic acid ester, 7-halo-2-(1-oxohexyl)heptanoic acid ester, etc.), or diesters (e.g. 7-halo-2-carbomethoxyheptanoic acid ester, 7-halo-2-carboethoxyheptanoic acid ester, 7-halo-2-carbopropoxyheptanoic acid ester, 7-halo-2-carbobutoxyheptanoic acid ester, 7-halo-2-carbopentyloxyheptanoic acid ester, 7-halo-2-carbohexyloxyheptanoic acid ester, etc.), and preferably, 7-chloro-2-(1-oxoethyl)heptanoic acid ester, 7-chloro-2-carboethoxyheptanoic acid ester, wherein "halo" is chloro or bromo.

$R^1$ for the above $\beta$-oxo-acid ester [II] is a straight chain or branched chain alkyl group such as methyl, ethyl, propyl, butyl, pentyl, hexyl, and the like. When the $\beta$-oxo-acid ester [II] is one of the above diesters, that is, when $R^2$ is a group of the formula: $OR^3$, it is preferable that $R^1$ and $R^3$ are the same.

The nitrosating agent [IV] used in the present reaction is, for example, nitrous acid alkyl esters (e.g. methyl nitrite, ethyl nitrite, propyl nitrite, butyl nitrite, pentyl nitrite, hexyl nitrite, heptyl nitrite, octyl nitrite, nonyl nitrite, decyl nitrite, etc.), halogenated nitrosyls (e.g. nitrosyl chloride, etc.), nitrosylsulfuric acid, or nitrous acid. The nitrous acid alkyl ester is preferably nitrous acid lower alkyl esters such as methyl nitrite, ethyl nitrite, propyl nitrite, butyl nitrite and the like.

Alternatively, the nitrous acid alkyl ester may be prepared in this reaction system and used therein. For example, a nitrous acid alkyl ester can be prepared by charging in advance a nitrous acid salt (e.g. sodium nitrite, potassium nitrite, etc.) and an alcohol (e.g. methanol, ethanol, propanol, butanol, pentanol, hexanol, etc.) into a reaction system, followed by adding thereto an acid to give a nitrous acid alkyl ester.

The nitrosating agent is usually used in an amount of 1 mol or more, preferably 1-3 mols, to 1 mol of the $\beta$-oxo-acid ester [II].

The reaction is usually carried out at a temperature of $-10°$ to $80°$ C., preferably $0°$ to $50°$ C. The reaction period is not necessarily specified, but usually in the range of 10 minutes to 24 hours.

In the above reaction, a solvent may be used. The solvent used therein may be any conventional one which does not inhibit the present reaction, for example, hydrocarbons (e.g. n-heptane, n-hexane, cyclohexane, etc.), halogenated hydrocarbons (e.g. 1,2-dichloroethane, etc.). When a nitrous acid alkyl ester is used as a nitrosating agent [IV], a corresponding alcohol may be used, that is, when n-butyl nitrite is used as a nitrosating agent [IV], n-butanol is used as a solvent.

In order to promote the above reaction, water or alcohol may additionally be used therein.

The 7-halo-2-hydroxyiminoheptanoic acid ester [III] produced by the above reaction may be isolated from the reaction mixture by a conventional procedure such as extraction or concentration, but may be used in the next reaction without isolation from the reaction mixture.

The next reaction of the 7-halo-2-hydroxyiminoheptanoic acid ester [III] and an aldehyde compound or a ketone compound for giving a haloketo acid derivative [I] is usually carried out in the presence of an acid. The acid may be any conventional inorganic or organic acid (e.g. hydrochloric acid, sulfuric acid, nitric acid, acetic acid, etc.). The amount of the acid is not necessarily specified, but is usually 0.001 mol or more, preferably 0.01 mol or more, to 1 mol of the β-oxo-acid ester [II]. However, when nitrosylsulfuric acid is used as a nitrosating agent, it is not necessary to use additional acid, because sulfuric acid is produced from the nitrosylsulfuric acid by the nitrosating reaction The aldehyde used in this reaction includes, for example, formalin, glyoxylic acid, glyoxal, acetaldehyde, propionaldehyde, and the like, and the ketone used therein includes, for example, diacetyl, and the like. The amount of the aldehyde or ketone is not necessarily specified, but is usually 1 to 5 mols to 1 mol of the β-oxo-acid ester [II].

The above reaction is usually carried out at a temperature of 0° to 70° C., preferably 5° to 40° C. The reaction period is not necessarily specified, but is usually in the range of 1 to 24 hours. This reaction may be carried out in a solvent. The solvent may be the same as ones used in the previous reaction.

After completion of the reaction, the desired haloketo acid derivative of the formula [I] is isolated from the reaction mixture by a conventional procedure such as extraction, separation, neutralization, distillation of solvent, and the like.

The β-oxo-acid ester of the formula [II] can be prepared by reacting a halopentane derivative of the formula [V]:

 [V]

wherein X is the same as defined above, Y is a halogen atom (when X is chlorine atom, Y is other than fluorine atom, and when X is bromine atom, Y is neither fluorine atom nor chlorine atom), or Y is methanesulfonyloxy group or p-toluenesulfonyloxy group, with a β-oxo-acid derivative of the formula [VI]:

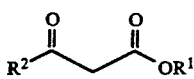 [VI]

wherein $R^1$ and $R^2$ are the same as defined above, in the presence of a base.

The halopentane derivative [V] used in the above reaction is, for example, dihalopentanes (e.g. 1,5-dichloropentane, 1-bromo-5-chloropentane, 1-iodo-5-chloropentane, 1,5-dibromopentane, 1-bromo-5-iodopentane, etc.), 5-halopentyl sulfonates (e.g. 5-chloropentyl methanesulfonate, 5-chloropentyl p-toluenesulfonate, etc.), among which the preferred ones are 1,5-dichloropentane, 1-bromo-5-chloropentane, 1-iodo-5-chloropentane, 5-chloropentyl methanesulfonate, and 5-chloropentyl p-toluenesulfonate.

The β-oxo-acid derivative [VI] includes, for example, 3-oxo-acid esters (e.g. acetoacetic acid ester, 3-oxopentanoic acid ester, 3-oxohexanoic acid ester, 3-oxoheptanoic acid ester, 3-oxooctanoic acid ester, etc.) or malonic acid diesters, preferably acetoacetic acid esters or malonic acid diesters.

$R^1$ in the formula [VI] is a straight chain or branched chain alkyl group (e.g. methyl, ethyl, propyl, butyl, pentyl, hexyl, etc.). When the β-oxo-acid derivative [VI] is a malonic acid diester, that is, when $R^2$ in the formula [VI] is a group of the formula: $OR^3$, it is preferable that $R^1$ and $R^3$ are the same.

In this reaction, the halopentane derivative [V] is used in the ratio of about 1 mole to 1 mole of the β-oxo-acid derivative [VI], but even though one of these is used in the excess amount to another one, this reaction is not disadvantageously affected thereby.

The base used in the above reaction includes, for example, sodium alkoxides (e.g. sodium methoxide, sodium ethoxide, etc.), potassium alkoxides (e.g. potassium methoxide, potassium tert-butoxide, etc.), alkali metal hydroxides (e.g. sodium hydroxide, potassium hydroxide, etc.), or alkali metal carbonates (e.g. sodium carbonate, potassium carbonate, etc.), and the like. The base is usually used in an amount of 1 mol or more, preferably 1-3 mols, to 1 mol of the halopentane derivative [V].

The above reaction may be carried out either in a solvent or without a solvent. The solvent includes, for example, alcohols (e.g. methanol, ethanol, isopropyl alcohol, etc.), aromatic solvents (e.g. toluene, xylene, etc.), halogenated aromatic solvents (e.g. chlorobenzene, o-dichlorobenzene, etc.), aliphatic solvents (e.g. n-hexane, n-heptane, cyclohexane, etc.), ketone solvents (e.g. methyl isobutyl ketone, etc.), and the like.

The reaction may usually be carried out at a temperature of 0° to 300° C., preferably 50° to 150° C. The reaction period is not necessarily specified.

When an alkali metal hydroxide is used as a base, it is occasionally better to carry out the reaction with removing the resulting water.

After completion of the reaction, the resulting salt is removed by filtration or by dissolving in water, extracting, and the solvent is distilled off to give the β-oxo-acid ester of the formula [II], which may optionally be purified, for example, by evaporation, but can be used in the next procedure without further purification.

The process of the present invention comprising reacting via a novel β-oxo-acid ester [II] and 7-halo-2-hydroxyiminoheptanoic acid ester [III] is novel and can give the desired haloketo acid derivative [I] advantageously on industrial scale.

The present invention is illustrated by the following Examples, but should not be construed to be limited thereto.

EXAMPLE 1

A mixture of ethyl acetoacetate [VI-1] (260.2 g, 2.0 mol), methyl isobutyl ketone (300 g) and 1-bromo-5-chloropentane [V-1] (311.0 g, 1.68 mol) is heated to 80°–90° C. Thereto is added anhydrous potassium carbonate (300 g), and the mixture is reacted at 80°–90° C. for 12 hours. To the reaction mixture is further added potassium carbonate (341.4 g), and the mixture is reacted for additional 6 hours. After completion of the reaction, the mixture is filtered, and the methyl isobutyl ketone layer is washed with water and concentrated under reduced pressure. The residue (398.6 g) contains ethyl 7-chloro-2-(1-oxoethyl)heptanoate (content; 70.8%, yield; 72.6%), which is purified by column chromatography to give pure ethyl 7-chloro-2-(1-oxoethyl)-heptanoate [II-1].

EXAMPLE 2

Ethanol (135 g) is added to ethyl 7-chloro-2-(1-oxoethyl)heptanoate [II-1] (684 g, 2.92 mol), and the mixture is cooled to 5° C. While keeping the temperature at 5° C., to the mixture is added dropwise 43.5% solution (941 g, 3.22 mol) of nitrosylsulfuric acid in sulfuric acid over a period of 1 hour. The mixture is stirred at 5° C. for 1 hour, and the temperature is raised to 20° C. Separately, toluene (1000 g) and 36% aqueous formalin solution (487 g, 5.84 mol) are charged in another flask, and the temperature thereof is kept at 20°–25° C. Thereto is added dropwise the above reaction solution over a period of 1 hour. After keeping at the same temperature for 2 hours, the toluene layer is collected from the mixture The toluene layer is neutralized with saturated aqueous sodium hydrogen carbonate solution, and the neutralized aqueous layer is removed. The toluene layer is washed with water and concentrated under reduced pressure to give ethyl 7-chloro-2-oxopentanoate [I-1] (501 g, 2.42 mol, yield; 83.0%).

EXAMPLE 3

Ethyl 7-chloro-2-(1-oxoethyl)heptanoate [II-1] (208 g, 0.886 mol) is cooled to 5° C. While keeping the temperature at 5° C., to the mixture is added dropwise a mixture of 43.5% solution (310.4 g, 1.06 mol) of nitrosylsulfuric acid in sulfuric acid and water (31.9 g) over a period of 1 hour. The mixture is stirred at 5° C. for 1 hour, and then, the temperature thereof is raised to 20° C. Separately, 1,2-dichloroethane (200 g) and 36% aqueous formalin solution (110.7 g, 1.33 mol) are charged in another flask, and the temperature thereof is kept at 20°–25° C. Thereto is added dropwise the above reaction mixture over a period of 1 hour. After keeping at the same temperature for 2 hours, the 1,2-dichloroethane layer is collected from the mixture. The 1,2-dichloroethane layer is neutralized with saturated aqueous sodium hydrogen carbonate solution, and the neutralized aqueous layer is removed The 1,2-dichloroethane layer is washed with water and concentrated under reduced pressure to give ethyl 7-chloro-2-oxopentanoate [I-1] (149 g, 0.721 mol, yield; 81.4%).

EXAMPLE 4

To methyl 7-chloro-2-(1-oxoethyl)heptanoate [II-2] (6.5 g, 0.0295 mol) is added n-heptane (50 g), and the mixture is cooled to 5° C. While keeping the temperature at 5° C., to the mixture is added dropwise a mixture of 43.5% solution of nitrosylsulfuric acid in sulfuric acid (25.0 g, 0.086 mol) and water (0.531 g) over a period of 1 hour. The mixture is stirred at 5° C. for 1 hour, and then, the temperature thereof is raised to 20° C. Separately, 36% aqueous formalin solution (15 g, 0.180 mol) is charged in another flask, and the temperature thereof is kept at 20°–25° C. Thereto is added dropwise the above reaction mixture over a period of 1 hour. After keeping at the same temperature for 1 hour, n-heptane (100 g) is added to the mixture, and the n-hepatane layer is collected from the mixture. The n-heptane layer is neutralized with saturated aqueous sodium hydrogen carbonate solution, and the neutralized aqueous layer is removed. The n-heptane layer is washed with water and concentrated under reduced pressure to give methyl 7-chloro-2-oxopentanoate [I-2] (3.4 g, 0.0176 mol, yield; 60%).

EXAMPLE 5

A mixture of ethyl acetoacetate [VI-1] (109.3 g), n-heptane (100 g) and 1-bromo-5-chloropentane [V-1] (185.5 g) is heated to 90° C. Thereto is added anhydrous potassium carbonate (193.5 g) in portions, and the mixture is stirred with heating at 100° C. for 14 hours. The mixture is filtered with suction, and the residue is washed with n heptane. The n-heptane layers (i.e. the above filtrate and washing liquid) are combined to give a solution (347 g) of crude ethyl 7-chloro-2-(1-oxoethyl)heptanoate [II-1] in n-heptane (content of the heptanoate; 44.3%).

The said solution (347 g) of crude ethyl 7-chloro-2-(1-oxoethyl)heptanoate [II-1] in n-heptane is cooled to 5° C., and thereto is added dropwise a mixture of 43.5% solution (227 g) of nitrosylsulfuric acid in sulfuric acid and water (12.7 g) over a period of 1 hour, while keeping the temperature at 5° C. Separately, 36% aqueous formalin solution (200 g) is charged in another flask, and the temperature thereof is kept at 20°–25° C. Thereto is added dropwise the above reaction mixture over a period of 1 hour. After keeping at the same temperature for 2 hours, water (400 ml) is added to the mixture, and the heptane layer is separated. The heptane layer is neutralized with saturated aqueous sodium hydrogen carbonate solution, and the neutralized aqueous layer is removed. The heptane layer is washed with water and concentrated under reduced pressure to give ethyl 7-chloro-2-oxopentanoate [I-1] [145.2 g, content; 82.0%, yield; 68.9% (to ethyl acetoacetate)].

EXAMPLE 6

A mixture of methyl acetoacetate [VI-2] (127.7 g, 1.1 mol) and methanol (200 g) is heated to 30° C. Thereto is added dropwise 28.1% solution of sodium methoxide in methanol (192 g, 1.0 mol), and the mixture is stirred for 1 hour. Thereto is added 1-bromo-5-chloropentane [V-1] (155.5 g, 0.838 mol), and the mixture is reacted at 70° C. for 2 hours. After completion of the reaction, the reaction mixture is concentrated under reduced pressure, and thereto is added toluene (500 g). The precipitated salt is removed by filtration. The toluene layer is washed with water and concentrated under reduced pressure to give methyl 7-chloro-2-(1-oxoethyl)heptanoate [II-2] (189.9 g, content; 88.7%, yield; 91.2%).

B.p.: 118°–120° C./0.6–0.7 mmHg

NMR (60 MHz, CDCl$_3$) $\delta$(ppm): 1.0–2.1 (m, 8), 2.2 (s, 3), 3.3–3.7 (m, 3), 3.8 (s, 3)

To the above obtained methyl 7-chloro-2-(1-oxoethyl)heptanoate [II-2] (43.3 g, content; 88.7%, 0.174 mol) are added sodium nitrite (36.0 g) and methanol (130 ml), and the mixture is cooled to 0° C. Thereto is added dropwise conc. sulfuric acid (51.2 g, 0.522 mol) over a period of 3 hours. Then, the mixture is stirred at 0° C. for 48 hours, and concentrated under reduced pressure. To the mixture are added toluene (200 g) and water (200 g), and the mixture is stirred. The toluene layer is taken, and dried over magnesium sulfate and concentrated. The concentrated reaction mixture is purified by column chromatography to give methyl 7-chloro-2-hydroxyiminoheptanoate [III-2] (25.8 g, yield: 71.5%).

NMR (60 MHz, CDCl$_3$) δ(ppm): 1.3-2.2 (m, 7), 2.5-2.9 (m, 2), 3.5 (t, 2, J=5.4 Hz), 4.9 (s, 3)

EXAMPLE 7

A mixture of ethyl acetoacetate [VI-1] (260.2 g, 2.0 mol), methyl isobutyl ketone (300 g) and 1-bromo-5-chloropentane [V-1] (311.0 g, 1.68 mol) is heated to 80°-90° C. Thereto is added anhydrous potassium carbonate (300 g), and the mixture is reacted at 80°-90° C. for 12 hours. To the reaction mixture is added potassium carbonate (341.4 g), and the mixture is reacted for additional 6 hours. After completion of the reaction, the methyl isobutyl ketone layer is washed with water, and concentrated under reduced pressure to give crude ethyl 7-chloro-2-(1-oxoethyl)heptanoate [II-1] (398.6 g, content; 70.8%, yield; 72.6%).

NMR (60 MHz, CDCl$_3$) δ(ppm): 1.0-2.1 (m, 13), 2.2 (s, 3), 3.2-4.7 (m, 3), 4.2 (q, 2, J=7.6 Hz)

EXAMPLE 8

A mixture of ethyl acetoacetate [VI-1] (260.6 g, 2.0 mol), toluene (300 g) and 1-bromo-5-chloropentane [V-1] (311.0 g, 1.68 mol) is heated to 80°-90° C. Thereto is added anhydrous potassium carbonate (300 g), and the temperature thereof is raised to 100° C. The mixture is reacted at the same temperature for 18 hours. After completion of the reaction, the mixture is filtered, and the toluene layer is washed with water, and concentrated under reduced pressure to give crude ethyl 7-chloro-2-(1-oxoethyl)-heptanoate [II-1] (403.8 g, content; 68.8%, yield; 69.1%).

EXAMPLE 9

A mixture of ethyl acetoacetate [VI-1] (218.6 g), n-heptane (200 g) and 1-bromo-5-chloropentane [V-1] (371.0 g, 2.0 mol) is heated to 90° C. Thereto is added anhydrous potassium carbonate (387 g, 2.8 mol), and the mixture is stirred with heating at 100° C. for 12 hours. The mixture is filtered with suction and the n-heptane layer is collected. The residue is washed with n-heptane (300 g), and the n-heptane layer is combined with the previous n-heptane layer, and concentrated under reduced pressure to give crude ethyl 7-chloro-2-(1-oxoethyl)heptanoate [II-1] (449.2 g), which contains 74.1% of ethyl 7-chloro-2-(1-oxoethyl)-heptanoate and 22.1% of 1-bromo-5-chloropentane.

Yield: 84.4% (to ethyl acetoacetate) Recovery rate (based on 1-bromo-5-chloropentane): 97.7%

The above obtained crude ethyl 7-chloro-2-(1-oxoethyl)heptanoate [II-1] (198.9 g, content; 74.1%, 0.63 mol) is cooled to 5° C. Thereto is added dropwise 43.5% solution of nitrosylsulfuric acid in sulfuric acid (220 g, 0.75 mol) over a period of 1 hour. Then, the mixture is stirred at 5° C. for 1 hour, and the temperature thereof is raised to 20° C. Separately, toluene (500 g), water (200 g) and sulfamic acid (10 g) are charged in another flask, and the mixture is kept at 10° C. Thereto is added dropwise the above reaction mixture. The mixture is stirred for 1 hour. The toluene layer is taken and neutralized with saturated aqueous sodium hydrogen carbonate solution, and the neutralized aqueous layer is removed. The toluene layer is washed with water and concentrated under reduced pressure to give ethyl 7-chloro-2-hydroxyiminoheptanoate [III-1] (124.3 g, yield; 89.3%).

M.p.: 36°-38° C.

NNR (60 MHz, CDCl$_3$) δ(ppm): 1.1-2.1 (m, 10), 2.3-3.9 (m, 2), 3.5 (t, 2, J=6.0 Hz), 4.3 (q, 2, J=7.0 Hz)

EXAMPLE 10

The solution of ethyl 7-chloro-2-hydroxyiminoheptanoate [III-1] in toluene obtained in Example 9 (without being concentrated) is added dropwise into 36% aqueous formalin solution, and thereto is added sulfuric acid. The mixture is warmed, and further thereto is added water. The organic layer is separated, neutralized, washed with water, and concentrated under reduced pressure to give ethyl 7-chloro-2-oxoheptanoate [I-1].

EXAMPLE 11

A 28% solution of sodium methylate in methanol (19.3 g) and methanol (50 g) are charged in a flask, and the mixture is cooled to 0° C. To the mixture is added dimethyl malonate (13.2 g) and the mixture is stirred at 50° C. for 1 hour. To the mixture is added 1-bromo-5-chloropentane (18.6 g) and stirred under refluxing for 14 hours. The reaction mixture is concentrated under reduced pressure, and to the residue are added toluene (200 g) and water (100 ml) and the mixture is further stirred. The organic layer is separated and magnesium sulfate (10 g) is added to the organic layer. The mixture is filtered and the filtrate is concentrated. Separately, a 43.5% nitrosylsulfuric acid solution (35.3 g) is charged in another flask and cooled to 0° C. To the mixture is added dropwise the above concentrated organic layer over a period of 1 hour. The mixture is stirred at 0° C. for 1 hour, and the temperature thereof is raised to 20° C. The mixture is stirred at the same temperature for 1 hour. Separately, toluene (100 g) and 10% aqueous formalin solution (100 g) are charged in another flask and cooled to 5° C. Thereto is added dropwise the above reaction mixture over a period of 1 hour. The reaction mixture is kept at 5° C. for 1 hour, and stirred at 20° C. for 12 hours. The organic layer is separated and washed with water, and to the mixture is added magnesium sulfate (5 g) and filtered. The filtrate is concentrated under reduced pressure to give crude methyl 7-chloro-2-oxoheptanoate (24 g), which is purified by distillation under reduced pressure to give methyl 7-chloro-2-oxoheptanoate (14.3 g).

What is claimed is:

1. A process for preparing a haloketo acid derivative of the formula:

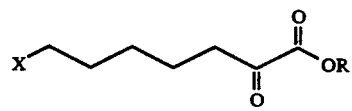

wherein R is hydrogen atom or an alkyl group having 1 to 6 carbon atoms, and X is chlorine atom or bromine atom, which comprises reacting a β-oxo-acid ester of the formula [II]:

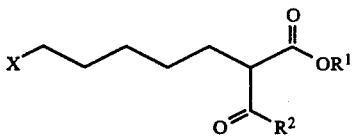

wherein $R^1$ is an alkyl group having 1 to 6 carbon atoms, $R^2$ is an alkyl group having 1 to 5 carbon atoms or a group of the formula: $OR^3$ (wherein $R^3$ is an alkyl group having 1 to 6 carbon atoms), and X is the same as defined above, with a nitrosating agent of the formula [IV]:

  [IV]

wherein $R^4$ is an alkyl group having 1 to 12 carbon atoms, or a group of the formula: $SO_3H$ to give 7-halo-2-hydroxyiminoheptanoic acid ester of the formula [III]:

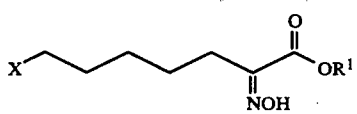

wherein $R^1$ and X are the same as defined above, followed by reacting the compound [III] with an aldehyde compound or a ketone compound in the presence of an acid.

2. The process according to claim 1, wherein X is chlorine atom, $R^1$ is ethyl group, and $R^2$ is methyl group or ethoxy group in the formula [II].

3. The process according to any one of claims 1 and 2, wherein the nitrosating agent [IV] is nitrosylsulfuric acid.

4. The process according to claim 1, wherein the β-oxo-acid ester of the formula [II]:

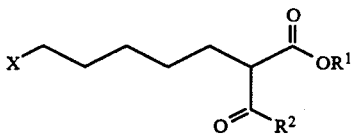

wherein $R^1$ is an alkyl group having 1 to 6 carbon atoms, $R^2$ is an alkyl group having 1 to 5 carbon atoms or a group of the formula: $OR^3$ (wherein $R^3$ is an alkyl group having 1 to 6 carbon atoms), and X is chlorine atom or bromine atom, is prepared by reacting a halopentane derivative of the formula [V]:

wherein X is the same as defined above, and Y is a halogen atom, provided that when X is chlorine atom, Y is other than fluorine atom, and when X is bromine atom, Y is neither bromine atom nor fluorine atom, or Y is methanesulfonyloxy group or p-toluenesulfonyloxy group, with a β-oxo-acid derivative of the formula [VI]:

$$\underset{R^2}{\overset{O}{\|}}\diagdown\diagup\underset{OR^1}{\overset{O}{\|}}$$  [VI]

wherein $R^1$ and $R^2$ are the same as defined above, in the presence of a base.

5. The process according to claim 4, wherein the halopentane derivative [V] is 1-bromo-5-chloropentane, and the β-oxo-acid derivative [VI] is an acetoacetic acid ester or a malonic acid diester.

6. The process according to claim 1, wherein the β-oxy-acid ester of formula [II] is selected from the group consisting of 7-halo-2-(1-oxoethyl)heptanoic acid ester, 7-halo-2-(1-oxopropyl)heptanoic acid ester, 7-halo-2-(1-oxobutyl)heptanoic acid ester, 7-halo-2-(1-oxopentyl)heptanoic acid ester, 7-halo-2-(1-oxohexyl)heptanoic acid ester, 7-halo-2-carbomethoxyheptanoic acid ester, 7-halo-2-carboethoxyheptanoic acid ester, 7-halo-2-carbopropoxyheptanoic acid ester, 7-halo-2-carbobutoxyheptanoic acid ester, 7-halo-2-carbopentyloxyheptanoic acid ester and 7-halo-2-carbohexyloxyheptanoic acid ester wherein the term halo is chloro or bromo.

7. The process according to claim 6, wherein the nitrosating agent [IV] is nitrosylsulfuric acid.

8. The process according to claim 1, wherein the nitrosating agent [IV] is selected from the group consisting of methyl nitrite, ethyl nitrite, propyl nitrite and butyl nitrite.

9. The process according to claim 1, wherein the nitrosating agent [IV] is prepared by combining a nitrous acid salt and an alcohol to form a first mixture, followed by adding to said first mixture an acid to form a nitrous acid alkyl ester.

10. The process according to claim 1, wherein the nitrosating agent [IV] is present in an amount of from 1 to 3 mols with respect to 1 mol of the β-oxo-acid ester [II].

11. The process according to claim 1, wherein the reaction of the β-oxo-acid [II] and the nitrosating agent [IV] is carried out in a temperature range of from −10° to 80° C.

12. The process according to claim 1, wherein the reaction of the β-oxo-acid [II] and the nitrosating agent [IV] is carried out in a temperature range of from 0° to 50° C.

13. The process according to claim 9, wherein the process further comprises the presence of an alcohol solvent corresponding to the nitrosating agent [IV].

14. The process according to claim 1, wherein the compound [III] is reacted with an aldehyde compound or a ketone compound in the presence of an acid, said acid being present in an amount of from 0.001 mol or more to 1 l mol of the β-oxo-acid ester [II].

15. The process according to claim 1, wherein the acid present during the reaction of the compound [III] and the aldehyde or ketone compound is selected from the group consisting of hydrochloric acid, sulfuric acid, nitric acid and acetic acid.

16. The process according to claim 1, wherein the aldehyde and ketone compounds are selected from the group consisting of formalin, glyoxylic acid, glyoxal, acetaldehyde, propionaldehyde and diacetyl.

17. The process according to claim 1, wherein the amount of the aldehyde or ketone compound present is 1 to 5 mols to 1 mol of the β-oxo-acid ester [II].

18. The process according to claim 1, wherein the reaction of the compound [III] and the aldehyde or ketone compound is carried out at a temperature of from 0° to 70° C.

19. The process according to claim 1, wherein the reaction of the compound [III] and the aldehyde or ketone compound is carried out at a temperature of from 5° to 40° C.

20. The process according to claim 4, wherein the halopentane derivative [V] is selected from the group consisting of 1,5-dichloropentane, 1-bromo-5-chloropentane, 1-iodo-5-chloropentane, 5-chloropentyl methanesulfonate, and 5-chloropentyl p-toluenesulfonate.

21. The process according to claim 4, wherein the β-oxo-acid derivative [VI] is an aceticoacetic acid ester or a malonic acid diester.

22. The process according to claim 4, wherein the β-oxo-acid derivative [VI] is a malonic acid diester such that $R^2$ is the group $OR^3$, and wherein $R^1$ and $R^3$ are the same.

23. The process according to claim 4, wherein the base is selected from the group consisting of sodium methoxide, sodium ethoxide, potassium methoxide, potassium tert-butoxide, sodium hydroxide, potassium hydroxide, sodium carbonate and potassium carbonate.

24. The process according to claim 4, wherein the base is present in an amount of 1-3 mols to 1 mol of the halopentane derivative [V].

25. The process according to claim 4, wherein the reaction of the halopentane derivative [V] and the β-oxo-acid derivative [VI] is carried out at a temperature of from 0° to 300° C.

26. The process according to claim 4, wherein the reaction of the halopentane derivative [V] and the β-oxo-acid derivative [VI] is carried out at a temperature of from 50° to 150° C.

* * * * *